United States Patent [19]

Spry

[11] Patent Number: 4,954,783
[45] Date of Patent: Sep. 4, 1990

[54] APPARATUS AND METHOD FOR TESTING MOISTURE OF EAR CORN

[76] Inventor: Robert H. Spry, 21 Sunset Rd., Bloomington, Ill. 61701

[21] Appl. No.: 398,714

[22] Filed: Aug. 28, 1989

[51] Int. Cl.$^5$ .................................................. G01R 27/22
[52] U.S. Cl. ...................................... 324/696; 324/724; 324/715; 324/694; 324/692; 73/73
[58] Field of Search ............... 324/692, 693, 694, 696, 324/713, 722, 724; 73/73

[56] References Cited

U.S. PATENT DOCUMENTS

| | | | |
|---|---|---|---|
| 1,987,244 | 1/1935 | Moore | 324/693 |
| 3,218,552 | 11/1965 | Asmann et al. | 324/693 |
| 3,427,537 | 2/1969 | Osborne | 324/65 R |
| 3,967,198 | 6/1976 | Gensler | 324/72 |
| 4,019,132 | 4/1977 | Loch | 324/65 R |
| 4,039,942 | 8/1977 | Glaser | 324/72 |
| 4,259,633 | 3/1981 | Rosenau | 324/65 R |
| 4,451,781 | 5/1984 | Anderson | 324/65 R |

OTHER PUBLICATIONS

Kang et al., "An Electronic Probe for Estimating Ear Moisture Content of Maize", Crop Science, vol. 18, Nov./Dec. '78, pp. 1083-1084.

*Primary Examiner*—Reinhard J. Eisenzopf
*Assistant Examiner*—Jack B. Harvey
*Attorney, Agent, or Firm*—Emrich & Dithmar

[57] ABSTRACT

A corn moisture tester is adapted to measure the moisture content of corn kernels on an ear of corn. The ear of corn may be affixed to the corn stalk. The device includes an ear cradle, a pair of electrode blades and circuit for measuring a moisture-dependent electrical property of the corn kernels. The cradle is adapted for receiving an ear of corn and includes two portions hinged together so they may be opened to receive the ear. When the cradle portions are closed, they form a substantially cylindrical interior cradle surface for engaging the ear of corn. The conductor blades are mounted to one portion of the cradle to pierce the kernels but not the cob when the cradle is closed about an ear under test. The electrical property measuring circuit generates and displays a signal representative of moisture.

17 Claims, 1 Drawing Sheet

APPARATUS AND METHOD FOR TESTING MOISTURE OF EAR CORN

BACKGROUND OF THE INVENTION

The present invention relates to electrical moisture testers for measuring the moisture content of corn kernels on an ear of corn (i.e., "ear corn").

Electrical moisture testers for measuring the moisture content of vegetable matter, and in particular grains, are well known in the art. Most moisture testers operate on the principal that the electrical properties (namely, resistance or resistivity) of vegetable matter vary with the moisture content of the matter.

Some moisture testers, especially those for measuring grains, are designed to take bulk measurements after the grain or other crop has been harvested and is in storage. Such devices are not as reliable with corn if they do not penetrate the kernel since the resistance of the pericarp of a corn kernel is not considered a reliable indicator of the moisture content of the corn.

Moreover, bulk measuring devices which require separation of the kernel from the plant may not be useful or convenient in helping a farmer determine when to harvest the crop, or a seed corn company in determining "dry down" time of a new hybrid seed under development.

A moisture tester designed to estimate the moisture content of corn kernels on the cob is disclosed in an article entitled *An Electronic Probe For Estimating Ear Moisture Content of Maize* (Kang, et al, *Crop Science*, Vol. 18, November–December 1978, pp. 1083-1084). That device uses a pair of spaced needle-shaped conductors which are applied to penetrate the husk, kernels and cob. The moisture meter then signals the relative magnitude of the electrical resistance of the cob, kernels and husk in contact with the needle conductors.

It is known that the relationship between cob moisture and the moisture content of corn kernels on the cob, varies substantially with different corn genotypes, different moisture levels, and even with the weather. Thus, cob moisture can not be generally correlated with corn kernel moisture. It is also known that the moisture content of the husk can influence the value of the moisture reading obtained, especially when a test is being made in the field while the ear is still on the plant.

SUMMARY OF THE INVENTION

The corn moisture tester of the invention measures the moisture content of corn kernels on an ear of corn. The ear of corn defines a longitudinal axis and has a cob and a plurality of corn kernels over the surface of the cob in a plurality of rows. The rows extend generally in the direction of the ear axis. The corn kernels have an exterior pericarp and an interior endosperm.

The present invention provides a corn moisture tester which is capable of measuring the moisture content of kernels of corn (without influence by the moisture content of the husk or cob) while those kernels are present upon a cob in an ear of corn. This permits in-field testing.

The present invention provides a corn moisture tester wherein the value of the signal generated by the signal means in the moisture meter is not influenced by the moisture content of the cob nor the husk of the ear of corn.

The invention includes a fixture having a pair of piercing conductor blades adapted for piercing corn kernels in such a manner that the blades penetrate the pericarp and rest in contact with the endosperm of a corn kernel. The blades have a configuration and orientation relative to the cradle which insures that each blade penetrates the pericarp of at least one kernel of corn without contacting the cob.

A pair of conductor blades are mounted in a cradle having an interior cradle surface adapted to receive an ear of corn. The moisture meter includes a pair of terminals connected to a resistance-measuring circuit and a display. The conductor blades are electrically connected to the terminals of the circuit. The circuit is adapted for measuring electrical resistance of the corn kernels when the conductor blades, which are a fixed distance apart, pierce at least one of the corn kernels on the cob.

In the embodiment disclosed herein, the cradle includes a fixed part in the form of a semi-cylinder which is adapted to receive an ear of corn. The fixed cradle sections which preferably extends about a major portion of the circumference of the ear; and it is mounted on a handle which houses both the measuring circuit and the display which is considered an advantage in use and enhances portability. The electrodes are mounted in the fixed cradle section, spaced a predetermined distance apart in an axial direction.

A second, moveable cradle section or cover which also may be semi-cylindrical is hinged to the fixed cradle section for swinging motion about an axis parallel to the axis of the ear to assist in embedding the active surfaces of the electrodes in the endosperm and not in the cob or the husk.

In operation, the farmer or technician, with the cradle in an open position, grasps the handle with one hand and places the ear in the fixed cradle section. He then uses his free hand, while still holding the handle with the other, to swing the hinged cradle cover into contact with the ear, forcing the ear into the electrodes so that the active surfaces of the electrodes pierce the kernels and establish electrical contact with the interior endosperm of the kernels. The reading is thus a measure of the electrical resistance between kernels spaced a fixed distance apart on an ear of corn. The display scale is calibrated to read percentage of moisture.

The moisture measurement of the instant invention is useful, not so much because of its definitive accuracy (which can be verified or confirmed in a laboratory setting), but because of its convenience, its ability to test in the field (with or without husking), and because it provides a reliable, repeatable quantitative measure with sufficient accuracy that a farmer may use it in determining when a particular field should be harvested. By properly testing the corn for harvest, a farmer may cut his expenses by eliminating the cost of drying the corn in an elevator.

For example, a farmer may test an ear on several plants at one time and mark those plants. He may then come back later and repeat the measurements. This will provide him with information on the rate of drying as well as the state of dryness (or moisture content). Because the instrument is compact and portable, a single person may take a number of measurements in different parts of a given field or in different fields to determine the proper time for harvest without the inconvenience of collecting a sample of the corn from different areas, labelling each sample, taking the samples to a laboratory and then correlating the lab data with the test sites.

Moreover, an important factor used by seed corn companies in selection of a new hybrid seed for commercial use is the rate of moisture loss as the plant matures. The present invention enables a geneticist or technician to take measurements of seed moisture in the field without husking the ear and without removing the ear from the plant. This enables the tester to return to take the same measurements on the same ears later to develop a more accurate history of moisture content versus maturity. Using adjacent plants (which is mandatory if the ears are removed and sent to a laboratory for testing) is not desirable since it introduces variables such as emergence, growth rate, and date of flowering in the measurements.

Moreover, seed corn producers frequently take field ear samples to schedule seed harvest. The present invention would enable producers to take these tests in the field with greater convenience and reliability.

Ear corn samples are also taken from ear corn wagons during the harvest campaign to identify incoming moisture for paying contract growers. With the present invention, tests for ear corn moisture could be quickly done and measurements representative of different parts of the load (and thus the field) could be taken to give a better measure of the value of a load of harvested corn.

Other features and advantages of the present invention will be apparent to persons skilled in the art from the following detailed description of a preferred embodiment accompanied by the attached drawing wherein identical reference numerals will refer to like parts in the various views.

BRIEF DESCRIPTION OF THE DRAWINGS

There is illustrated in the accompanying drawings a preferred embodiment of the corn moisture tester of the invention which, when considered in connection with the following detailed description, the invention, its construction and operation, and many of its advantages will be readily understood and appreciated.

DETAILED DESCRIPTION OF THE INVENTION

Figure 1:
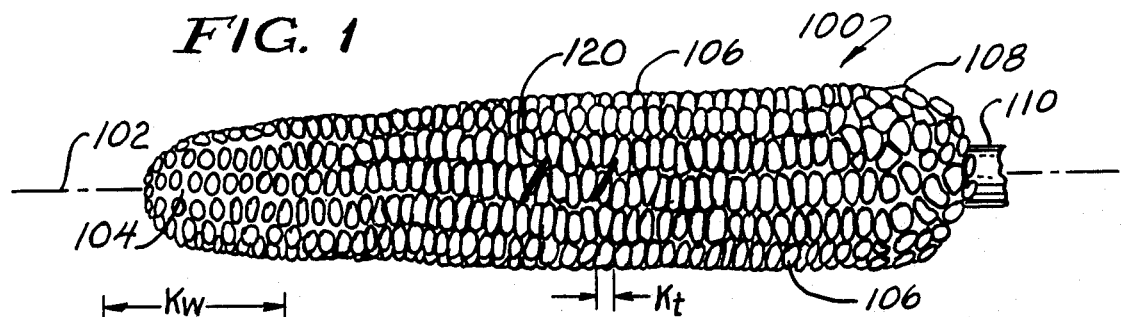
FIG. 1 is a side elevation of an ear of corn having the husk removed therefrom and illustrating the manner in which the conductor blades of the corn tester of the invention insure penetration of at least one corn kernel each.

Referring now to the drawings, and in particular FIG. 1, there is illustrated an ear of corn generally indicated by reference numeral 100. The ear of corn 100 defines a longitudinal ear axis 102 and comprises: a cob 104; a plurality of kernels 106, present on the cob 104 in a plurality of rows 108 which run generally parallel to the ear axis 102; and a husk which, for purposes of clarity in illustrating the invention, is not shown. Reference numeral 110 illustrates a fragment of the shank of the ear of corn. The measurement may be made with the ear removed or while it is still on the plant. The husk may be removed or not. The advantage of not removing the husk is that if the husk is removed, that ear cannot be used for testing later since exposure to air will change the dry-down rate.

Figure 2:
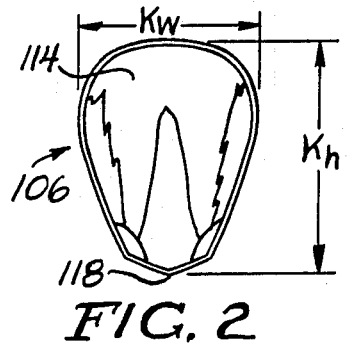
FIG. 2 is an enlarged front elevation of a corn kernel taken from the ear of corn illustrated in FIG. 1 and shown in longitudinal cross section.

FIG. 2 shows that the corn kernels 106 include an exterior pericarp 112 and an interior endosperm 114. The individual kernels 106 have a cross-sectional configuration resembling an inverted tear drop and therefore define a top portion 116 and bottom portion 118 where the kernel 106 is affixed to the cob 104. Thus, from top 116 to bottom 118, the corn kernel 106 has an overall height $K_h$, and from side to side a width of $K_w$. Likewise, each corn kernel has a thickness $K_t$ associated therewith (FIG. 1).

FIG. 1 shows that the size and shape of the individual corn kernels 106 varies, in a general manner, with the position of the kernel along the longitudinal ear axis 102. The size and shape of the individual corn kernels 106 is also slightly variable in a random manner, at any position on the ear 100. In general, however, the size of any individual kernel 106 is largest in the butt section adjacent the stalk 110 and smallest at the tip of the ear 102. Nonetheless, the variations in height $K_h$, width $K_w$ and thickness $K_t$ are not great. But the height, width and thickness are usually less at tip than at the butt of an ear.

Figure 3:
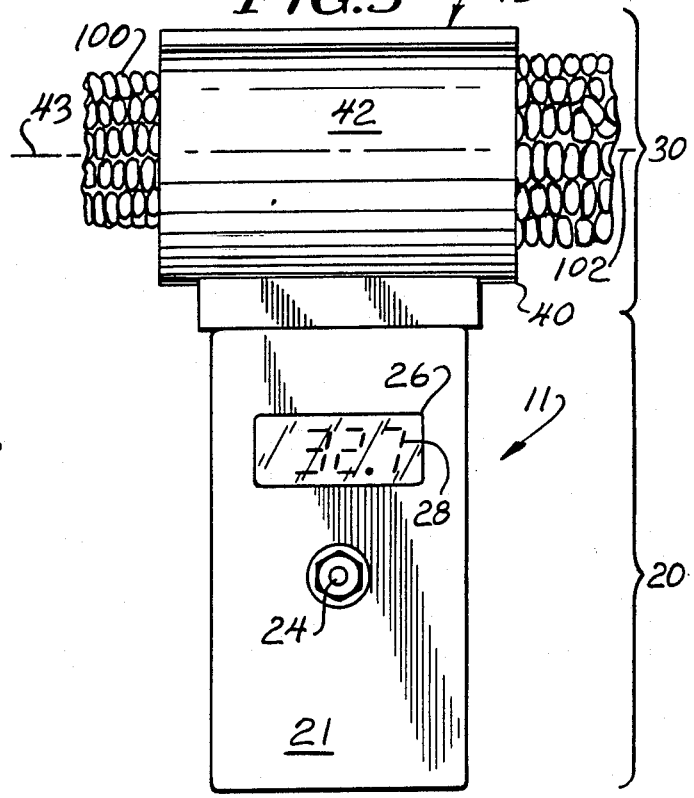
FIG. 3 is a front elevation of the corn moisture tester of the invention, illustrating how an ear of corn (in fragmentary view) is received in the cradle thereof to measure the moisture content of the corn kernels.
Figure 4:
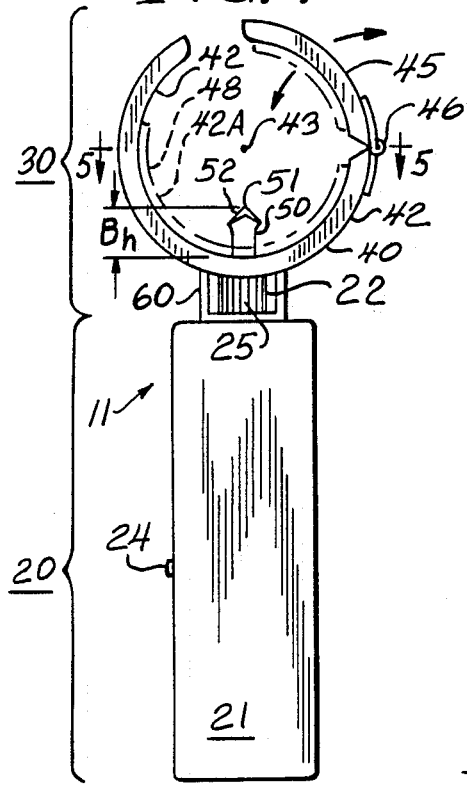
FIG. 4 is a side elevation of the corn moisture tester illustrated in FIG. 3, without the ear of corn.
Figure 5:
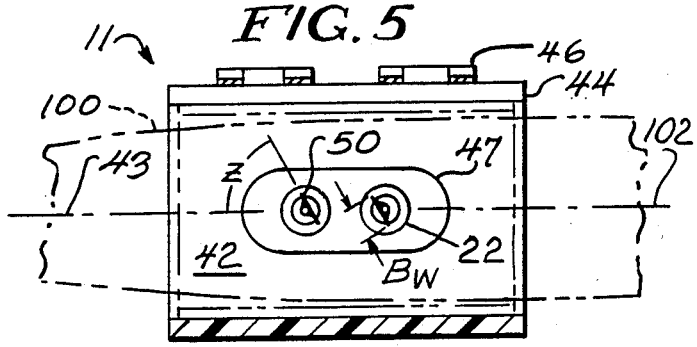
FIG. 5 is a plan view of the corn moisture tester of FIGS. 3 and 4, shown in partial cross-section and having the fragmentary view of the ear of corn illustrated in out line only, to show the novel configuration and orientation of the conductor blades of the invention.

Referring now to FIGS. 3, 4 and 5 there is shown a preferred embodiment of the corn moisture tester of the invention, generally indicated by reference numeral 11. The corn moisture tester 11 comprises a moisture meter 20, adapted for measuring the moisture content of corn or other vegetable matter, and a fixture 30 which includes a cradle 40, a pair of conductor blades 50, and a bracket 60 for mounting the cradle 40 to the housing 21 of the meter 20 so that the meter housing also acts as a handle.

The moisture meter 20 may be a commercially available instrument supplied by Delmhorst Instrument Company of Towaco, N.J. The unit 20 is described as a DHM-1 hay moisture meter and functions upon the principal that the electrical resistance of vegetable matter is a function of the moisture content of the vegetable matter. Accordingly, the moisture meter includes an electrical circuit for applying a predetermined voltage between a pair of terminals 22 (FIG. 5). The moisture tester 20 includes a switch 24, mounted to the handle 21, which, when actuated, applies a voltage across the terminals 22. Conductor blades 50 are mounted in the cradle 40 and electrically connected respectively to terminals 22.

Thus, if vegetable matter, such as corn kernels, is placed between and in electrical communication with conductor blades or electrodes 50, the voltage across terminals 22 will cause current to flow therebetween, through the vegetable matter. The magnitude of the current is a measure of the resistance of the vegetable matter, and it gives, when displayed on meter 26, a quantitative measure of the moisture content of the matter. Meter 26 is illustrated in the form of a digital read-out which displays a visual indication illustrated at 28 which is calibrated to indicate moisture percentage, rather than current, which the meter actually measures. The signal is, therefore, a useful quantitative representation of the moisture content of the vegetable matter.

While most moisture meters measure electrical resistance between a pair of fixed points, other circuit means may be employed to measure other moisture-dependent properties of corn.

As seen in FIGS. 4 and 5 the electrode blades 50 preferably are flat, thin blades, similar to conventional knife blades used for crafts and hobbies, including a sharp point 51 and knife edges 52 in the form of a chevron when viewed from the side, but honed to a sharp cutting edge. Preferably, the base of each blade 50 (i.e., the portion other than the honed edges) is covered with an electrically non-conducting material or coating so that only the chevron-shaped cutting edge is in electrical contact with the endosperm when the electrodes are embedded in the kernels. Thus, the cutting edges are the only active portions of the electrodes. An alternative electrode construction is an electrode in the form of a needle having a sharpened point providing the active area of the electrode, and the remainder of the needle being coated with an insulating material. The blade shape is preferred over the needle because it insures that at least one row of kernels will be pierced; whereas with a needle, the needle may be placed in an interstice between kernels, requiring re-placement before a reading can be taken.

By way of example, for the chevron blade electrode illustrated, the width of the active area may be about one-eighth of an inch, and the base of each electrode is covered with an insulating coating for a distance of at least three-eighths of an inch from the inner surface of the cradle. The electrodes 50 are adapted for piercing the pericarp 112 of a kernel of corn 106 and establishing electrical continuity with the endosperm 114 thereof over a substantial area. The electrodes 50 are fixedly mounted to the terminals 22 of the moisture tester 20 by soldering and the terminals may be mounted to the cradle by suitable insulating potting compound.

The ear cradle 40 includes a fixed cradle section 42 adapted to receive an ear of corn 100 as illustrated in FIGS. 3 and 5. The fixed cradle section is mounted to the handle 41. It has a substantially cylindrical configuration and thereby defines a longitudinal cradle axis 43. When an ear of corn 100 is received in the cradle section 42 the longitudinal axis 102 of the ear of corn 100 and the longitudinal cradle axis 43 are substantially aligned.

The cradle 40 also includes a moveable cradle section or cover 45 mounted to the fixed cradle section 42 by hinge means 46. The hinged cradle cover 45 is opened to permit an ear of corn 100 to be received in the cradle means 40. Thereafter, closing the hinged cradle cover 45 forces the ear of corn 100 onto the piercing electrodes 50 causing each of the electrodes 50 to each pierce at least one of the kernels 106 On the ear of corn 100. The depth of penetration of the conductor blades 50 is limited by the ear of corn 100 abutting the interior surface of the fixed cradle section 42. The electrodes 50 could also be mounted to the inside of hinged cover 45 in the same manner as electrodes 50 are mounted to cradle 40.

Although the hinged cradle cover 45 is not necessary to obtain the desired measurements, it is helpful when holding the handle in one hand, to close the cover 45 with the other hand. This insures that the ear will contact the concave surface 42 of the fixed cradle portion and that, in turn, insures proper penetration depth of the active surfaces of the electrodes.

The cradle 40 which may be fabricated from a section of rigid tubular insulating material is fixedly secured to the moisture meter 20 by mounting bracket 60, in the form of a short, U-shaped section of PVC channel glued to the cradle base 44. The mounting means 60 has holes formed therein. The terminals 22 include a threaded terminal stud (not shown) that is passed the holes. A threaded terminal cap 25, screwed over the studs secures the cradle means 40 to the moisture meter 20.

FIG. 5 shows that the terminals 22, and the conductor blades 50 affixed thereto, pass through an opening 47 formed in the cradle base 44. Thus, the conductor blades 50 are in fixed spacial relation to the interior cradle surface 42.

It is considered important that the configuration and orientation of the conductor blades 50 relative to the interior surface of cradle section 42 and cradle axis 43, insure that each conductor blade will pierce the pericarp and contact the endosperm of at least one kernel of corn, without contacting the cob, when the ear of corn is properly placed in the cradle 42.

FIG. 5 illustrates that the conductor blades 50 each define a blade plane oriented at a predetermined angle Z with respect to the cradle axis 53. Furthermore, the conductor blades 50 define a predetermined blade width $B_w$. FIG. 4 shows that because the conductor blades are in fixed relation with the interior cradle surface 42 projecting inwardly, a predetermined height $B_h$ above the surface 42.

To prevent the conductor blades 50 from piercing the cob 104 the predetermined blade height $B_h$ should be less than the kernel height $K_h$. For ear corn in the field, kernel moisture may vary widely from ear moisture depending on the state of maturity and the weather.

Referring once again to FIG. 1 there is illustrated a pair of perforations 120, created in an ear of corn 100 by the conductor blades 50 of the moisture tester of the invention 11. It should be noted that the configuration and orientation of the conductor blades 50 with respect to the cradle axis 43 insures that when an ear of corn 100 engages the concave inner surface of the fixed cradle section 42, each of the electrodes 50 bridges at least two rows of kernels 108 and straddles at least two adjacent kernels 106. Thus, each conductor blade 50 penetrates the pericarp and contacts the endosperm of at least one of the kernels 106 on the cob 100. Because the active surfaces of the electrodes 50 projects inwardly a predetermined distance from the surface of cradle section 42, the blades 50 penetrate the corn kernels 106 without penetrating the underlying cob 104. Thus, as the moisture meter 20 applies a constant voltage across terminals 22, only the electrical resistance of the corn kernels, and not the cob nor the husk, is measured.

To insure that each electrode blade 50 bridges at least two rows of kernels and straddles at least two adjacent kernels, the predetermined blade width $B_w$ and predetermined blade angle Z are chosen accordingly. Thus, the component of blade width, $B_w$, which projects in a direction substantially parallel to the cob axis 102, must be greater than the thickness $K_t$ of at least one kernel. Likewise, that component of blade width which projects in a direction substantially normal to the cob axis must be greater than the width of at least one kernel.

FIG. 4 shows that the cradle means 40 may include an optional cradle liner 48 for use when testing the moisture of husked ears. The liner 48 provides a new interior cradle surface 42A which changes the depth of penetration of the blades. The cradle liner or spacer 48 is removable and has a thickness approximately equal to the thickness of the husk on an ear of corn. Thus, moisture tester 11 can be used to measure the moisture of ears that have not been husked when the spacer is removed, and for husked corn when the spacer is inserted.

It will be appreciated that while the foregoing description of the corn moisture tester of the invention includes specific details as to elements such as a moisture tester, such details are for the purpose of illustrating the invention and not intended as a limitation of the scope thereof. Persons skilled in the art will be able to modify some of the structure which has been illustrated and to substitute equivalent elements for those disclosed while continuing to practice the principle of the invention; and it is, therefore, intended that all such modifications and substitutions be covered as they are embraced within the spirit and scope of the appended claims.

What is claimed is:

1. A corn moisture tester for measuring the moisture content of corn kernels on an ear of corn, said ear of corn defining a longitudinal ear axis and having a cob and a plurality of said corn kernels over the surface of said cob in a plurality of rows, said rows extending in the general direction of said ear axis and each of said kernels having an exterior pericarp and an interior endosperm, said moisture tester comprising:

a moisture tester for vegetable matter having a pair of terminals, meter means for measuring an electrical property of said matter, and a visual display;

cradle means for receiving and partially enveloping an ear of corn;

a pair of electrodes held by said cradle means at a fixed spacing and in electrical communication with said terminals, said electrodes being constructed and arranged such that each electrode pierces the pericarp of at least one of said kernels and is in electrical contact with the endosperm of at least one kernel, without contacting said cob when said ear of corn is received in said cradle;

said display generating a signal representative of the moisture content of said corn.

2. The corn moisture tester of claim 1 further including a removable insulating spacer within said cradle, said spacer being the approximate thickness of a husk of an ear of corn, whereby said tester may be used without having to remove the husk.

3. The corn moisture tester of claim 1 wherein said cradle means further comprises a fixed section having an interior cradle surface and a cradle cover hingedly affixed to said fixed section, said cradle cover being adapted to urge said ear of corn into abutting contact with said interior cradle surface to insure proper depth of said electrodes in the kernels of said ear.

4. The corn moisture tester of claim 1 wherein said cradle defines an inner concave surface adapted to engage said ear, and said electrodes each define an active surface spaced inwardly of said concave surface a predetermined height sufficient to contact the endosperm of corn kernels on a cob but not the cob itself when the outer surface of said ear contacts said concave surface of said cradle.

5. The corn moisture tester of claim 4 wherein said predetermined height is less than the height of a corn kernel.

6. The apparatus of claim 4 wherein each of said electrodes is a flat blade having a chevron-shaped cutting edge defining said active surface of said electrode, and the base of each electrode is covered with non-conducting material.

7. The apparatus of claim 4 wherein each of said electrodes includes at least one needle electrode having a point defining said active surface, and the base of each electrode is covered with insulating material.

8. The corn moisture tester of claim 1 further comprising a removable spacer of generally constant thickness and conforming to the interior concave surface of said cradle means, said spacer being the approximate thickness of the husk of an ear of corn, whereby said tester may be used on unhusked corn without said spacer, and on husked corn when said spacer is inserted.

9. The corn moisture tester of claim 1 wherein said cradle means includes an interior cradle surface and each of said electrodes defines an active surface spaced a predetermined height from said interior cradle surface the remainder of said electrodes being covered with non-conducting material whereby when an unhusked ear is inserted in said cradle the husk is electrically insulated from said electrodes when said ear of corn is received in said cradle means.

10. The apparatus of claim 9 wherein each of said electrodes is characterized as a blade having a thickness substantially less than its associated height and depth, a surface of each blade defining a plane, said blades being mounted in said cradle such that the planes thereof are parallel and define an angle with the axis of said cradle less than 90°.

11. The apparatus of claim 10 wherein the angle between the axis of said cradle and the planes of said blades is approximately 45°.

12. Apparatus for measuring the moisture content of corn kernels of an ear of corn, comprising: a handle adapted to be held in the hand of a user; a fixed cradle section mounted to said handle and defining a concave inner surface adapted to receive and engage an ear of corn in partial wrapping engagement, said fixed section having a length extending at least partially along the axis of said ear and extending a substantial portion about the periphery of said ear; a cover; means for mounting said cover to said fixed section for hinging motion between an open position and a closed position, said fixed section and said cover cooperating when said cover is in said open position to receive said ear of corn and cooperating when said cover is closed to secure the ear of corn in said cradle by engaging opposing surfaces of the periphery of said ear; a pair of electrodes mounted in one of said fixed section and cover and spaced a predetermined distance from each other, said electrodes defining conducting active surfaces constructed and arranged to pierce said kernels of corn when said cover is moved to said closed position and to establish electrical contact only with the endosperm of at least one kernel on said cob without contacting the cob itself, said electrodes being covered with non-conducting material except for said active surfaces; measuring means housed in said handle for generating a signal representative of the moisture content of said corn between said electrodes when said active surfaces of said electrodes are in testing relation with kernels of an ear of corn; and display means mounted in said handle for displaying indicia representative of the moisture content of said corn.

13. The apparatus of claim 12 wherein said fixed section of said cradle is a generally semi-cylindrical shape and is adapted to fit about an ear of corn received therein for a major portion of the periphery of said ear and where said fixed section and said cover cooperate to substantially fully encompass an ear when said cover is moved to the closed position.

14. The apparatus of claim 12 wherein said electrodes are blades having a height less than the height of a kernel of corn intended to be measured, and a width at least as great as the width of a kernel of corn intended to be measured as it is seated on an ear and a thickness substantially less than either the height or the width.

15. The apparatus of claim 14 wherein each of said blades defines a surface plane, the surface planes of said conductor blades being substantially parallel to one another and each defining an acute angle with the axis of a corn cob received in said fixed cradle section.

16. The apparatus of claim 15 wherein said acute angle is approximately 45°.

17. A method of measuring the moisture content of the kernels on an ear of corn without having to remove the ear from the plant comprising: placing a rigid cradle having a generally semi-cylindrical shape and a concave inner surface adapted to fit about a major portion of the periphery of said ear and extending along the axis thereof; holding said cradle in place about said ear by means of a handle; forcing said ear radially of said cradle by means of a cover hinged to said cradle, thereby forcing said ear into the cradle and causing a pair of blade electrodes having active surfaces to pierce corn kernels on said ear, limiting the penetration of said blade electrodes to insure said active surfaces do not contact the cob of said ear but do contact the endosperm of respective kernels of corn of said ear; measuring the electrical resistance between said blade electrodes; and displaying a signal representative of said resistance, and thereby being a quantitative measure of the moisture content of said corn, on a display incorporated in said handle.

* * * * *